(12) United States Patent
Da Fonseca

(10) Patent No.: US 10,330,589 B2
(45) Date of Patent: Jun. 25, 2019

(54) BINDING ASSAY SIGNAL ANALYSIS

(71) Applicant: BIOSURFIT, S.A., Aviero (PT)

(72) Inventor: João Manuel de Oliveira Garcia Da Fonseca, Azambuja (PT)

(73) Assignee: Biosurfit, S.A., Aveiro (PT)

( * ) Notice: Subject to any disclaimer, the term of this patent is extended or adjusted under 35 U.S.C. 154(b) by 0 days.

(21) Appl. No.: 15/928,148

(22) Filed: Mar. 22, 2018

(65) Prior Publication Data

US 2018/0209896 A1    Jul. 26, 2018

Related U.S. Application Data

(63) Continuation of application No. 15/659,253, filed on Jul. 25, 2017, which is a continuation of application (Continued)

(30) Foreign Application Priority Data

Oct. 6, 2014  (GB) .................................. 1417640.8
Oct. 6, 2014  (PT) .................................. 107946 A

(51) Int. Cl.
| | |
|---|---|
| *G01N 21/05* | (2006.01) |
| *G01N 21/25* | (2006.01) |
| *G01N 21/552* | (2014.01) |
| *G01N 21/64* | (2006.01) |
| *G01N 33/543* | (2006.01) |
| *G01N 21/00* | (2006.01) |
| *G01N 33/00* | (2006.01) |

(52) U.S. Cl.
CPC ............. *G01N 21/05* (2013.01); *G01N 21/25* (2013.01); *G01N 21/253* (2013.01); *G01N 21/552* (2013.01); *G01N 21/554* (2013.01); *G01N 21/64* (2013.01); *G01N 21/6452* (2013.01); *G01N 33/543* (2013.01); *G01N 21/00* (2013.01); *G01N 33/00* (2013.01)

(58) Field of Classification Search
CPC ........ G01N 21/05; G01N 21/25; G01N 21/64; G01N 21/552; G01N 33/543; G01N 33/00; G01N 21/00
See application file for complete search history.

(56) References Cited

U.S. PATENT DOCUMENTS

| | | |
|---|---|---|
| 2003/0027327 A1 | 2/2003 | Cunningham et al. |
| 2004/0005582 A1 | 1/2004 | Shipwash |
| (Continued) | | |

FOREIGN PATENT DOCUMENTS

| | | |
|---|---|---|
| WO | WO 03/048736 A2 | 6/2003 |
| WO | WO 2004/084708 A2 | 10/2004 |
| (Continued) | | |

OTHER PUBLICATIONS

Homola (Chem Rev. 2008, 108, 462-493) (Year: 2008).*
(Continued)

*Primary Examiner* — Sally A Merkling
(74) *Attorney, Agent, or Firm* — Patterson Thuente Pedersen, P.A.

(57) ABSTRACT

Methods for determining a sample concentration of target entities in a sample, for example, determining a concentration of target antigens or antibodies in a blood sample or other biological sample.

21 Claims, 6 Drawing Sheets

Related U.S. Application Data

No. 15/517,228, filed as application No. PCT/EP2015/073036 on Oct. 6, 2015.

(56) References Cited

U.S. PATENT DOCUMENTS

| | | | |
|---|---|---|---|
| 2009/0087925 A1* | 4/2009 | Wagner | B01F 5/061 436/518 |
| 2012/0142554 A1* | 6/2012 | Zhang | G01N 33/543 506/9 |
| 2013/0078620 A1 | 3/2013 | Gandini et al. | |

FOREIGN PATENT DOCUMENTS

| | | |
|---|---|---|
| WO | WO 2011/007138 A1 | 1/2011 |
| WO | WO 2011/017436 A1 | 2/2011 |
| WO | WO 2011/122972 A2 | 10/2011 |
| WO | WO 2012/131556 A1 | 10/2012 |

OTHER PUBLICATIONS

Foley et al., "Concentration Gradient Immunoassay. 2. Computational Modeling for Analysis and Optimization", Analytical Chemistry, vol. 79, No. 10, May 1, 2007, pp. 3549-3553.

Homola, "Surface Plasmon Resonance Sensors for Detection of Chemical and Biological Species", Chem. Reve. 108, 2008, pp. 462-493.

Smith et al., "Conceptual and statistical issues in the validation of analytic dilution assays for pharmaceutical applications", J of Biopharmaceutical Statistics, vol. 8, No. 1, Jan. 1, 1998, pp. 509-532.

PCT International Search Report for PCT/EP2015/073036, dated Jan. 20, 2016, 6 pages.

PCT Written Opinion for PCT/EP2015/073036, dated Jan. 20, 2016, 8 pages.

Portuguese Search Report for Portuguese Application No. 107946 A, dated Dec. 5, 2017, 8 pages.

Application and File History for U.S. Appl. No. 15/517,228, filed Apr. 6, 2017. Inventor: Da Fonseca.

Application and File History for U.S. Appl. No. 15/659,253, filed Jul. 25, 2017. Inventor: Da Fonseca.

* cited by examiner

BINDING ASSAY SIGNAL ANALYSIS

RELATED APPLICATIONS

This application is a continuation of U.S. application Ser. No. 15/659,253, filed Jul. 25, 2017, which is turn is a continuation of U.S. application Ser. No. 15/517,228, filed Apr. 6, 2017, which is a National Phase entry of PCT Application No. PCT/EP2015/073036, filed Oct. 6, 2015, which claims priority from Great Britain Application No. 1417640.8, filed Oct. 6, 2014, and which claims priority from Portuguese Application No. 107946 A, filed Oct. 6, 2014, the disclosures of which are hereby incorporated by referenced herein in their entirety.

FIELD OF THE INVENTION

The present disclosure relates to methods and systems for determining a concentration of target entities in a sample, for example, determining a concentration of target antigens or antibodies in a biological sample.

BACKGROUND OF THE INVENTION

Immunoassays can be used to quantitatively determine a concentration of target entities, for example antigens, present in a sample. In the case of microfluidic immunoassays, an arrangement comprising a microfluidic chamber into which a sample is introduced may be used. Such a chamber comprises a plurality of probe entities, for example antibodies, immobilized on a surface of the chamber such that, as the sample is passed over the surface, antigens in the sample bind to the antibodies in the chamber. The amount of antibody-antigen binding may be detected and quantified using, for example, fluorescence or surface plasmon resonance measurements (SPR) and a concentration of target entities in the sample can be determined from this amount.

Due to the constraints inherent in existing immunoassays, for example the probe density or detection sensitivity, the range of concentrations of target entities in a sample which can be detected by known microfluidic immunoassays is limited. For any one assay, detection and quantification will only work in a sensitive (ideally linear) range of the relationship between target concentration and detection signal. Below this range, signal to noise ratios are too low and above this range the assay saturates. In either case, the measured signal becomes independent of sample concentration.

It would be desirable to provide methods and systems for determining target concentration that address these issues and extend the dynamic range over which concentrations can be quantified.

SUMMARY OF THE INVENTION

In a first aspect a method is provided for determining a sample concentration of target entities in a sample, for example, determining a concentration of target antigens or antibodies in a blood sample or other biological sample. The method comprises obtaining assay data comprising data points of respective local measurements indicative of a local concentration of target entities immobilised at each of a plurality of assay areas of an assay assembly from an assay using the assay assembly. The assay areas are connected in series such that a sample flowing through the assay assembly flows past each assay area in sequence. Each assay area comprises a plurality of probe entities immobilized at a surface of the assay area, the probe entities being arranged to bind to the target entities in the sample, such that the concentration of the target entities is depleted as the sample flows from one of the assay areas to the next. The assay data is modeled with a parameterized function of the local measurements against a quantity indicative of the position of the respective assay areas in the sequence, wherein one or more of the parameters are dependent on the sample concentration. A value indicative of the sample concentration is determined based on at least one of the one or more parameters.

By using depletion data obtained from a plurality of serially connected assay areas, information concerning target-probe binding can be obtained at different concentrations of target entities as the concentration decreases from one assay area to the next. Accordingly, a larger range of sample concentrations of target entities can be determined as compared to a system comprising a single assay area. By modeling the data with a function of measurement results from the plurality of assay areas against the quantity, the data is combined so that the overall signal to noise ratio may be improved.

It will be understood that modeling the data may involve adjusting the one or more parameters to fit the parameterized function to the data points, for example by reducing or minimizing a corresponding sum function capturing a discrepancy between values of the parameterized function and the data points, as is well known in the art. Examples of such known techniques are non-linear regression, gradient descent and least square optimization in general.

In some embodiments, one of the one or more parameters is a variable parameter indicative of an offset amount which offsets the quantity indicative of the position of the assay area in the sequence such that the parameterized function is a function of the local measurements against the quantity indicative of the position of the assay area in the sequence offset by the offset amount. In other words, where the quantity indicative of the position of the assay area, i, in the sequence is denoted by $DZ_i$, the parameterized function is a function of ($DZ_i$+Offset), where 'Offset' is the offset amount.

The parameterized function may be derived from a plurality of assay data sets, each obtained for a respective sample concentration, the sample concentrations covering a range of sample concentrations.

The parameterized function may be thought of by way of illustration to aid understanding and not limitation, as representative of a master depletion curve defining the depletion of a concentration of a target entities in a system characteristic of the assay assembly, the system comprising a plurality of notional assay areas arranged such that the concentration of target entities is depleted from one notional assay area in the sequence to the next notional assay area in the sequence. The number of notional assay areas is greater than the number of assay areas in the assay assembly. The fit of the master depletion curve to the assay data sets can be thought of by notionally offsetting the assay areas by the offset amount such that the assay areas of the assay assembly are mapped to a set of notional assay areas corresponding to a sample concentration.

The parameterized function may be a logistic function. In some cases an $n^{th}$ order polynomial function or a spline may be used, or any other suitable functional form may be used.

The parameterized function may comprise a look up table to represent the master depletion curve, for example, using interpolation to construct data points between data entries in the look up table.

In some embodiments, the offset amount is determined by minimizing a difference between the respective local measurement and a corresponding value of the parameterized function for each assay area of the assay assembly. For example, the offset amount may be determined using a least squares approximation or any other suitable approximation.

In some embodiments, the offset amount, 'Offset' is determined by minimizing the following function:

$$\sum_{i=1}^{n}[DP(DZ_i) - f(DZ_i + \text{Offset})]^2$$

where $DP(DZ_i)$ is the local measurement at the respective assay area, i, and $f$ is the corresponding value of the parameterized function. As previously described, $DZ_i$ is the quantity indicative of the position of the assay area in the sequence. Minimization of any suitable cost function may be carried out to obtain the best fit of the parameterized function to the assay data. For example, Chi-squared minimization techniques may be used. Other minimization approaches may be to apply a weighting to the local measurements. For example, a lower weighting might be given to measurements close to a noise threshold. For example, a higher weighting may be given to the assay areas earlier in the sequence.

In some embodiments, the one or more parameters may comprise one or more fixed parameters characteristic of a given assay assembly. For example, one fixed parameter may be indicative of a maximum amplitude of the local measurement which can be detected from the assay area sometimes referred to as $DP_{max}$ below. For example, another fixed parameter may be indicative of an amount by which or a rate at which the concentration of target entities is depleted as the sample flows from one assay area to the next, sometimes referred to as Shape below. It will be appreciated that these parameters are referred to as fixed in the sense that they are characteristic of an assay assembly (or a batch or assay assemblies manufactured under substantially identical conditions) and substantially do not vary as a function of the composition of the sample to by assayed. It will be understood that each assay assembly is only used once in some embodiments and hence experiments are carried out using respective assay assemblies from the same manufacturing batch to characterise the batch. The determined fixed parameters may be verified as being representative of the batch by validation experiments using other assemblies of the batch with samples of known sample concentration or target entities.

The values of $DP_{max}$ and Shape may be determined and fixed for the assay assembly.

The one or more fixed parameters may be determined using experimental data, for example, by minimizing a difference between the respective local measurement and a corresponding value of the parameterized function for each assay area, i, in the assay assembly for each of a plurality of experiments, j, wherein each experiment is carried out using a sample having a given concentration of target entities and the concentrations span a range of concentrations. For example, the offset amount may be determined using a least squares approximation or any other suitable approximation.

In one example, the one or more fixed parameters or set of constants, λ, may be determined by minimizing the following function $$\sum_{j=1}^{m}\sum_{i=1}^{n}[DP(DZ_i) - f_\lambda(DZ_i + \text{Offset}_j)]^2$$

Wherein data from m experiments is used and wherein, for each experiment, an assay assembly comprising n assay areas is used. In addition to the fixed parameters, a value of 'Offset' can also be determined for each of the plurality of experiments, j. Using this data, a relationship between Offset and the starting concentration of target entities of a sample for each experiment, Concentration$_j$, may be defined as a calibration function giving a concentration value for a corresponding value of Offset. For example, a calibration function can be fitted to data points of {Concentration$_j$, Offset$_j$}. As will be described further below, the calibration function may be used to determine the sample concentration of target entities based on at least one of the one or more the variable parameters, in particular Offset in the example above.

The parameterized function may be a logistic function.

In some embodiments, the parameterized function is proportional to:

$$\frac{DP_{max}}{1 + \exp[\text{Shape} \times (DZ_i + \text{Offset})]} \quad (1)$$

wherein $DP_{max}$ is indicative of a maximum amplitude of the local measurement which can be detected from an assay area, Shape is indicative of a rate at which the concentration of target entities is depleted as the sample flows from one assay area to the next, Offset is a variable parameter determined by data fitting, and $DZ_i$ is indicative of the position of the respective assay area, i, in the sequence.

In some embodiments, detection is carried out in the centre of each assay area, accordingly $DZ_i$ may take a positive half integer value for each assay area i.e. 0.5, 1.5, 2.5, etc. This is because an amount of depletion occurs in the first assay area prior to the locus where the first measurement is taken. $DZ_i$ may take an integer value, or any other suitable value. In some embodiments a mixture of integer and half integer values may be used. In some embodiments, the quantity indicative of position in the sequence is indicative of an amount of probe entities (able to interact with target entities) present upstream of the assay area—the locus where the corresponding measurement is taken. In these embodiments, the change in the quantity from one assay area to the next may be non-constant and may depend on the amount of probe entities or the capacity to bind target entities between the two assay areas concerned.

The parameterized function may be fit to the obtained assay data by adjusting the value of Offset. This, by way of illustration, can be thought of as mapping the assay data to the master depletion curve. The value indicative of the concentration of target entities in the sample may be determined using a value of Offset with a calibration function.

In the parameterised function given by (1) above, the assay assembly is characterized by determining $DP_{max}$ and Shape. More complex models, for example the 4PL and 5PL functions mentioned below may be more accurate in describing the system however, in such complex models, additional fitting parameters are used.

The value indicative of the sample concentration may be determined, for example calculated, using a calibration function. The calibration function may be a logistic function, an exponential function, or any other suitable function. In some embodiments the calibration function comprises a first function for use at sample concentrations of a target entity above a given value, and a second function for use at sample concentrations of a target entity below the given value. In a particular embodiment the first function is a function of Offset, and the second function is a function of a notional undepleted response at $DZ_i=0$ such that the second function is a function of:

$$\frac{DP_{max}}{1 + \exp[\text{Shape} \times \text{Offset}]} \quad (4)$$

Determining the value indicative of the sample concentration of the target entities may comprise calculating the sample concentration itself or calculating any transformation of the sample concentration. Likewise, determining the value indicative of sample concentration may include modeling the local measurements directly or any transformation thereof.

Determining the sample concentration may be an iterative process. For example, a first step may be applied initially followed by a second step that may provide a more refined result. Specifically, in some embodiments, the first function is used in the first step to determine a value indicative of concentration. If the value is below a threshold, the second step re-calculates the value using the second calibration function. In some embodiments, the order is reversed and the first function is used in the second step if the value from the first step (from the second function) is above a threshold.

In some embodiments, the calibration function is a 4 parameter logistic (4PL) nonlinear regression model as shown in equation (2) below:

$$y = d + \frac{a-d}{1+\left(\frac{x}{c}\right)^b} \quad (2)$$

where a, b, c and d are fixed parameters and x=Offset (or other fit parameter).

In some embodiments, the calibration function is a 5 parameter logistic (5PL) nonlinear regression model as shown in equation (3) below.

$$y = d + \frac{(a-d)}{\left(1+\left(\frac{x}{c}\right)^b\right)^g} \quad (3)$$

where a, b, c, d and g are fixed parameters and x=Offset (or other fit parameter).

As mentioned above, the 4PL and 5PL functions can also be used as the parameterized function. In that case, $x=DZ_i+$Offset, for example.

In some embodiments each local measurement is indicative of variation in a refractive index at the surface of the respective assay area due to target-probe binding. For example, the local measurement may correspond to a change in Surface Plasmon Resonance (SPR) behavior at the detection area. Such a change may be detected by a change in the peak of SPR absorption, for example, a diffusion angle value at which the peak occurs. Other SPR detection paradigms, for example based on wavelength or phase may of course be used in some embodiments. Using SPR measurements, changes in the local concentration of target entities from one assay area to the next of 0.5 nM may be detected. Alternatively, any other suitable means for quantitatively detecting an amount of target-probe binding at the surface of the respective assay area may be used, for example, fluorescence or absorption detection (for example UV absorption) and/or detection of a label (fluorescent or otherwise) bound to the target entities may be used.

Variation in the refractive index at the surface of the respective assay area may be amplified using an amplifier solution, in some embodiments. The amplifier solution is arranged to interact with target entities bound to the surface of the assay area such that the variation in the refractive index at the respective assay area is amplified when the amplifier has interacted with the bound target entities. The amplifier solution may comprise entities which are arranged to bind to the target entities which are in turn bound to the surface of the assay area, for example gold nanoparticles that are functionalized to bind to the target entities to give target specific amplification, other suitable nanoparticles, secondary antibodies, and beads may be used. The amplifier solution may amplify the variation in the refractive index at the surface of the respective assay area by 2-20 times, for example 5-10 times, for example 10 times.

The target and/or probe entities may be molecules or other suitable entities, for example proteins, DNA, peptides, enzymes, viruses, bacteria, cells, etc. The sample may be a blood sample or any other liquid biological (or other) sample.

In some embodiments, each local measurement comprises a difference between a baseline signal detected prior to interaction of the sample with the assay area and a post-amplification signal detected after interaction of the amplifier solution with target entities bound to the respective assay area. For example, the post-amplification signal may be detected after the respective assay area has been washed with a buffer solution.

In some embodiments, each local measurement comprises a difference between a pre-amplification signal and post-amplification signal. The pre-amplification signal is detected after interaction of the sample with the respective assay area and before interaction of the amplifier solution with target entities bound to the respective assay area. The post-amplification signal is detected after interaction of the amplifier solution with target entities bound to the respective assay area. The pre-amplification signal may comprise a contribution from a bulk sample refractive index of the sample. The post-amplification signal may be obtained after unbound amplifier and the sample have been substantially washed away by buffer solution in a wash step subsequent to the application of amplifier. In such embodiments, the parameterized function of the local measurements may comprise an adjustment term to account for the bulk sample refractive index of the sample affecting the pre-amplification signal but not the post-amplification signal. The adjustment term may be fit to the data points as part of the one or more variable parameters, for example it may be fit simultaneously together with Offset in some embodiments. In other embodiments, the adjustment term may be determined based on a difference between a baseline signal detected prior to interaction of the sample with the assay area and the pre-amplification signal. In such embodiments there is no need to fit this term but rather the adjustment term can simply be subtracted from the local measurement (the difference between the pre and post amplification signals).

Using local measurements which comprise a difference between the pre-amplification signal and post-amplification signal has the advantage that the local measurement is made over a shorter time period and so the effect of any drift in the signals being compared is reduced. Embodiments that account for bulk sample refractive index contribution to the pre-amplification signal advantageously dispense with the need for a separate wash step prior to amplification if bulk sample refractive index changes are to be accounted for.

In some embodiments, the concentration of amplifier solution is such that the assay assembly (i.e. all assay areas) is saturated with amplifier.

In some embodiments, the concentration of amplifier solution is such that the assay assembly is not saturated with amplifier. In such embodiments, the local measurements are dependent on the concentration of the amplifier solution as well as the concentration of target in the sample. Hence, there is a combined depletion effect from both the sample concentration and from the amplifier itself. These two distinct depletion processes may be characterized by the parameterized function, for example, the parameterised function may contain an additional parameter to account for the depletion of amplifier or an additional term. Alternatively or in addition, the 'Shape' parameter may be a vector varying with both the sample concentration and the amplifier concentration. In some embodiments, Shape may be a function of the quantity indicative of position/upstream binding capacity to capture the varying concentration of amplifier. In some embodiments, the effect of the concentration of amplifier can be thought of as being akin to the effect of the density of probe entities present in the assay assembly. Accordingly, for example, the value of $DZ_i$ may be adjusted to account for the amplifier concentration in a similar way to how $DZ_i$ is adjusted to take into account the relative binding capacity of the assay assembly as will be described in detail below.

Using amplifier in non-saturating conditions has the advantage that reduced amounts of amplifier are required, hence cost is reduced.

In some embodiments the assay areas have the same binding capacities for the target entities.

In some embodiments the assay areas have different binding capacities for the target entities. In some embodiments, $DZ_i$ is indicative of an amount of probe entities upstream of the position of the assay assembly, i.

The assay areas may be connected by microfluidic circuitry. In some embodiments, the circuitry between the assay area as a binding capacity for target entities.

Each assay area may be located in a respective chamber connected to adjacent chambers housing respective assay area(s) in the sequence by a conduit between pairs of chambers. Each assay area may occupy a portion of a chamber, wherein the local measurements are made at each respective portion. Alternatively, the assay area may occupy the whole chamber. In some embodiments, a plurality of assay areas is provided in a single chamber, for example as part of a contiguous functionalized surface, the assay areas being solely defined by the locus where measurements are taken.

Each local measurement may be indicative of a rate at which the amplifier solution interacts with the respective assay area, for example measured as a rate of change of the measurement signal at a defined point.

Each local measurement may comprise a measurement indicative of the time taken from introduction of the amplifier solution into the respective assay area to detection of a threshold signal amplitude, for example a maximum signal amplitude.

In some embodiments, obtaining assay data may comprise carrying out the local measurements. Alternatively, assay data may be obtained from a third party.

In a second aspect a system for determining a sample concentration of target entities in a sample is provided. The system comprises a processor arranged to obtain assay data comprising data points of respective local measurements indicative of a local concentration of target entities immobilized at each of a plurality of assay areas of an assay assembly from an assay using the assay assembly, wherein the assay areas are connected in series such that a sample flowing through the assay assembly flows past each assay area in sequence, and wherein each assay area comprises a plurality of probe entities immobilized at a surface of the assay area, the probe entities being arranged to bind to the target entities, such that the concentration of the target entities is depleted as the sample flows from one of the assay areas to the next. The processor is also arranged to model the assay data with a parameterized function of the local measurements against a quantity indicative of the position of the respective assay areas in the sequence, wherein one or more of the parameters are dependent on the sample concentration. The processor is further arranged to determine a value indicative of the sample concentration based on at least one of the one or more parameters.

In a third aspect a method for determining a sample concentration of target entities in a sample is provided. The method comprises introducing a sample into an assay assembly from an assay using the assay assembly, the assay assembly comprising a plurality of assay areas wherein the assay areas are connected in series such that a sample flowing through the assay assembly flows past each assay area in sequence, and wherein each assay area comprises a plurality of probe entities immobilized at a surface of the assay area, the probe entities being arranged to bind to the target entities, such that the concentration of the target entities is depleted as the sample flows from one of the assay areas to the next. The sample is caused to flow through the assay assembly and local measurements are carried out at each assay area to obtain assay data comprising data points of respective local measurements indicative of a local concentration of the target entities immobilized at each of the plurality of assay areas of the assay assembly. The assay data is modeled with a parameterized function of the local measurements against a quantity indicative of the position of the assay area in the sequence, wherein one or more of the parameters are dependent on the sample concentration. A value indicative of the sample concentration is determined based on at least one of the one or more parameters.

In a further aspect, a system is provided for determining a sample concentration of target entities in a sample. The system comprises an assay assembly comprising a plurality of assay areas connected in series such that a sample flowing through the assay assembly flows past each assay area in sequence, and wherein each assay area comprises a plurality of probe entities immobilized at a surface of the assay area, the probe entities being arranged to bind to the target entities, such that the concentration of the target entities is depleted as the sample flows from one of the assay areas to the next. The system further comprises at least one detector arranged to carry out local measurements at each assay area to obtain assay data comprising data points of respective local measurements indicative of a local concentration of the target entities immobilized at each of the plurality of assay areas. The system further comprises a processor arranged to model the assay data with a parameterized function of the local measurements against a quantity indicative of the position of the assay area in the sequence, wherein one or more of the parameters are dependent on the sample concentration. The processor is also arranged to determine a value indicative of the sample concentration based on at least one of the one or more parameters.

In some embodiments a single detector is provided for carrying out local measurements at the plurality of assay areas, for example by moving one of the detector and the assay areas relative to the other. Alternatively, a detector may be provided for each assay area.

In a further aspect, a method for determining a sample concentration of target entities in a sample is provided. The method comprising obtaining assay data comprising a local measurement indicative of a local concentration of the target entity immobilised at an assay area of an assay assembly from an assay using the assay assembly, wherein the assay area comprises a plurality of probe entities immobilized at a surface of the assay area, the probe entities being arranged to bind to target entities. The local measurement is based on signals indicative of a variation in a refractive index at the surface of the assay area, such variation being amplified following interaction of an amplifier solution with target entities bound to the surface of the assay area. The local measurement comprises a difference between a pre-amplification signal and post-amplification signal, wherein the pre-amplification signal is detected after interaction of the sample with the assay area and before interaction of the amplifier solution with the target entities bound to the assay area, and the post-amplification signal is detected after interaction of the amplifier solution with the target entities bound to the assay area and after the assay area has been washed with a buffer solution. The method further comprises adjusting the local measurement using an adjustment term such that a bulk sample refractive index of the sample is taken into account and using the adjusted local measurement to determine a value indicative of the sample concentration.

In some embodiments, the adjustment term is determined based on a difference between a baseline signal detected prior to interaction of the sample with the assay area and the pre-amplification signal. The features relating to the compensation for bulk sample refractive index contribution of the bulk of the sample described above are equally applicable here.

In a further aspect an assay assembly for determining a sample concentration of target entities in a sample is provided. The assay assembly comprises a plurality of assay areas serially connected such that a sample flowing through the assay assembly flows through each assay area in sequence. Each assay assembly comprises an inlet and an outlet and for each pair of assay areas in the plurality of assay areas, the outlet of a first assay area is coupled to the inlet of a second assay area by a coupling portion, such that a sample flowing through the assay assembly flows from first assay area to the second assay area via the coupling portion for each pair of assay areas in the plurality of assay areas. In addition, each assay area comprises a plurality of probe entities immobilized at a surface of the assay area, the probe entities being arranged to bind to the target entities, such that the concentration of the target entities is detectably depleted as the sample flows from one of the assay areas to the next.

As a sample is passed through the assay assembly, the flow of the sample may be a laminar flow such that diffusion or other mixing effects are substantially negligible. In such cases, only target entities in a portion of the sample adjacent the chamber surface will be available for binding with the probe entities. As the sample passes from one chamber to the next sufficiently fast to limit diffusion, due to the laminar flow of the sample, the same portion of sample will be adjacent the surface of each chamber and only target entities present in that same portion of the sample are available for binding. Hence, the concentration of target entities in the portion of the sample adjacent each surface is depleted as the sample flows from one chamber to the next. While the depletion may be only a small fraction of the amount of target in the bulk of the sample, due to diffusion limited laminar flow the depletion of target entities represents a significant detectable change in concentration.

In a further aspect, a microfluidic device comprising an assay assembly described above is provided.

It will be appreciated that each of the features described above may apply to each aspect described. All possible combinations are not listed in detail here for the sake of brevity.

BRIEF DESCRIPTION OF THE DRAWINGS

Specific embodiments are described below by way of example only and with reference to the accompanying drawings in which.

DETAILED DESCRIPTION OF THE INVENTION

Figure 1:
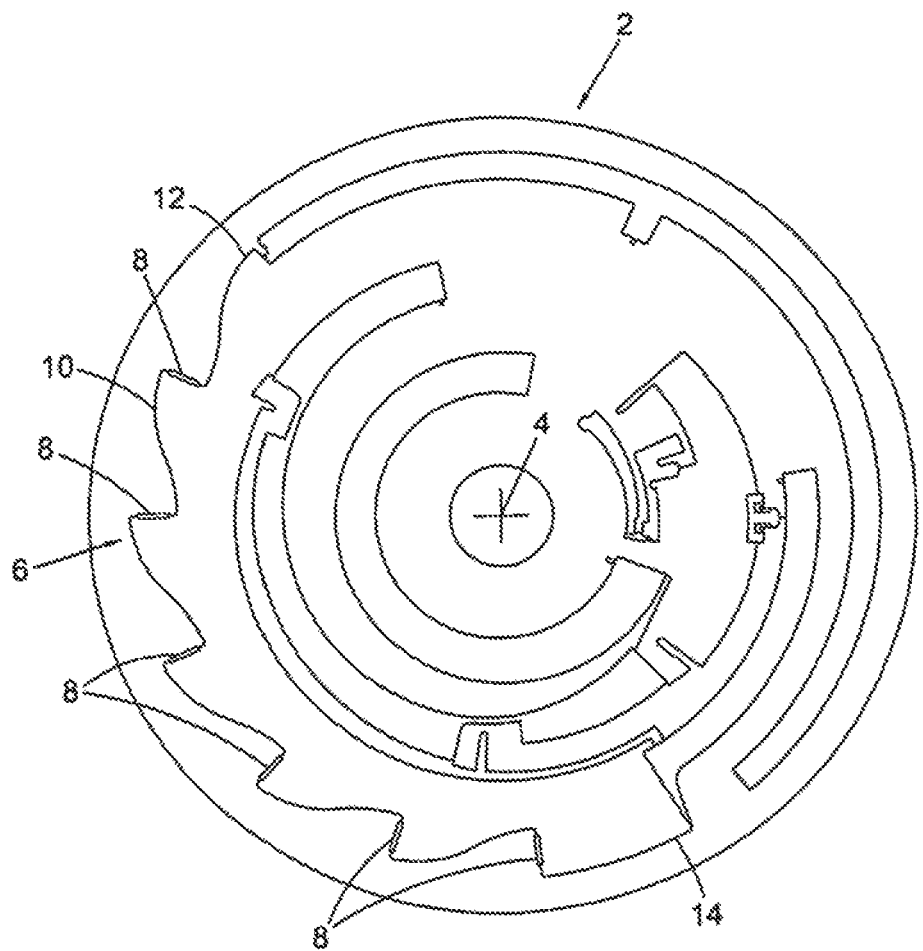
FIG. 1 is a schematic illustration of a device comprising an assay assembly.

With reference to FIG. 1, a centrifugal or "lab on a disc" microfluidic device 2 is arranged for rotation about an axis 4. Typically, the microfluidic device 2 is a microfluidic polycarbonate disc having an outer diameter of 120 mm, a thickness of ~1.2 mm, and a hole in the centre of the disc measuring 15 mm in diameter. The disc comprises two 0.6 mm discs bound together by a thin-film polymer. The microfluidic features shown in FIG. 1 and described below are defined in one of the discs and the thin film. The other of the two discs comprises SPR areas provided with a gold coated diffraction grating as described below. The disc 2 comprises an assay assembly 6 which has a plurality chambers 8 arranged in series such that each pair of chambers in the plurality is linked by a conduit 10. The chambers are aligned with SPR areas. A sample, for example blood or other liquid, is introduced into the assay assembly 6 via an inlet conduit 14, which forms an inlet for the first chamber 8 in the series, and the sample leaves the assay assembly via an outlet conduit 12, which forms an outlet for the final chamber 8 in the series. Each chamber 8 measures 0.02 mm in depth and is placed at a distance of 50 mm from the centre of the disc. Each chamber is typically approximately 50 nl in volume and the assay assembly and device are arranged such that approximately 100 µl of liquid can flow through the assay assembly in approximately 5-6 minutes.

Figure 2A:
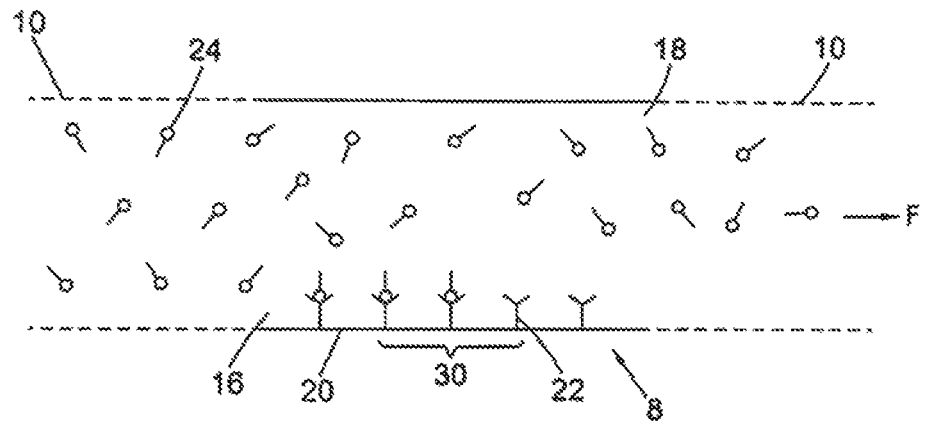
FIG. 2A is a schematic illustration of a cross-sectional view of target-probe binding in an assay area of the assay assembly of FIG. 1.

With reference to FIG. 2A, a single chamber 8 will now be described. The chamber 8 comprises an inlet 16 through which a sample may enter the chamber 8 from a connecting conduit 10 (or the inlet conduit 14 in the case of the first chamber in the series) and an outlet 18 through which the sample may leave the chamber 8 via a connecting conduit 10 (or the outlet conduit 12 in the case of the final chamber in the series). When a sample is passed through the chamber, the sample flows through the chamber from the inlet 16 to the outlet 18 in the direction shown by the arrow 'F' in FIG. 2A.

The chamber 8 has a surface 20 comprising a grating of sinusoidal shape (not shown) measuring 100 nm in height and having a period of 1600 nm. The surface 20 is gold coated and has a monolayer of probe entities 22 immobilized on top of the gold surface. Each probe entity 22 has the ability to specifically bind to a specific corresponding target entity 24 which may be present in a sample passed through the chamber 8, such that when a sample containing target entities 24 flows through the chamber 8, specific target entities 24 in the sample bind to the probe entities 22 at the chamber surface 20.

As a sample is passed through the assay assembly, the flow of the sample is a laminar flow at sufficient rate such that diffusion or other mixing effects are substantially negligible throughout the assay assembly. Accordingly, only target entities 24 in a portion of the sample adjacent the chamber surface 20 will be available for binding with the probe entities 22. As the sample passes from one chamber 8 to the next, due to the laminar flow of the sample, the same portion of sample will be adjacent the surface 20 of each chamber 8, hence only target entities 24 present in that same portion of the sample are available for binding. In this way, the concentration of target entities 24 in the portion of the sample adjacent each surface 20 is depleted as the sample flows from one chamber 8 to the next.

Due to probe entities in only a thin layer being available for binding, a concentration change in target entities bound to the probe entities from one chamber to the next is detectable using SPR technology. For example, a detectable change in concentration in the liquid layer adjacent the surface 20 may be 0.5 nM from one point in a chamber 8 to a corresponding point in the next chamber 8.

Figure 3:
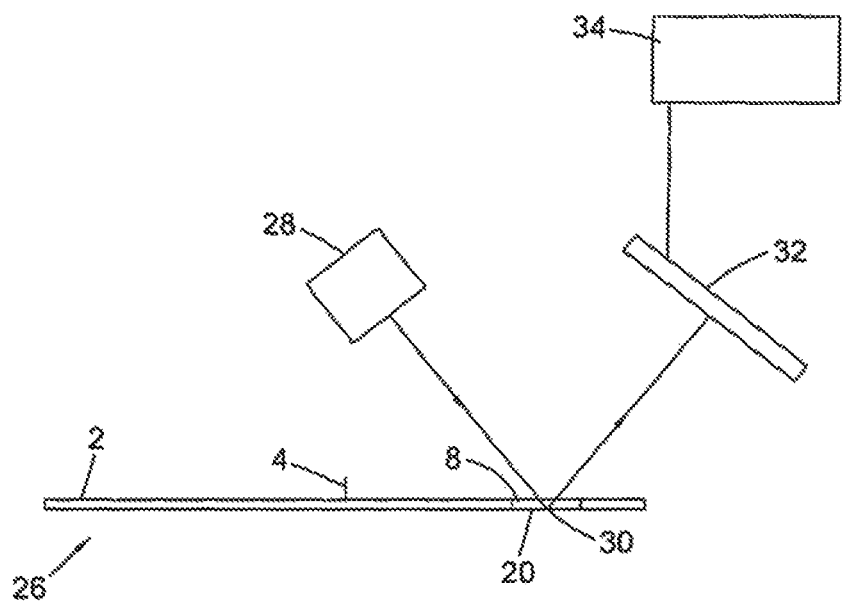
FIG. 3 is a schematic illustration of a system for determining the concentration of a target entity in a sample.

With reference to FIG. 3, a system 26 for determining the concentration of a target entity 24 in a sample is now described. The system 26 comprises a microfluidic device 2 comprising an assay assembly 6 as described above. A light source 28 is provided and aligned such that emitted light is incident on a detection zone 30 of the surface 20 a chamber 8. Typically the light source 28 is a polarized monochromatic light source, for example a diode laser. When in use, an amount of light incident on the detection zone 30 is reflected from the surface 20 and the reflected light is detected by a detector 32. The detector 32 is arranged to measure the light intensity of the reflected light beam as a function of angle over time.

The system further comprises a drive for rotating the device 2 to drive liquid flow in the device 2, under the control of a controller, such that various liquids including a sample are introduced into the device 2 and flow through the assay assembly 6 in a defined sequence. The drive is not illustrated in FIG. 3 for the sake of clarity but further details of how liquid flows may be controlled can be found in WO 2011/122972 and WO2012/131556, incorporated herein by reference.

When in use, changes in the refractive index at the surface 20 of the detection region 30 due to the presence of bound target entities or a bound target-amplifier complex (see below) cause changes in the resonant behavior of the surface 20, specifically changes in surface plasmon resonance behaviour. This can be detected by detecting a change in the angle at which a light intensity minimum occurs in the reflected light as a function of time. The binding of target entities 24 to probe entities 22 at the surface 20 of the chamber 8 causes a change in the refractive index at the surface 20. Accordingly, the amount of target-probe binding at the surface 20 of the chamber 8 can be quantitatively determined by detection of changes in the refractive index at the chamber surface 20, for example by detecting change in the angle at which surface plasmon resonance occurs. In some embodiments, alternative approaches for determining surface plasmon effects may be used. Examples of SPR measurement techniques are given in: Jiri Homola, "*Surface Plasmon Resonance Sensors for Detection of Chemical and Biological Species*", Chem. Rev. 108, pages 462-493 (2008), incorporated herein by reference.

Figure 4:
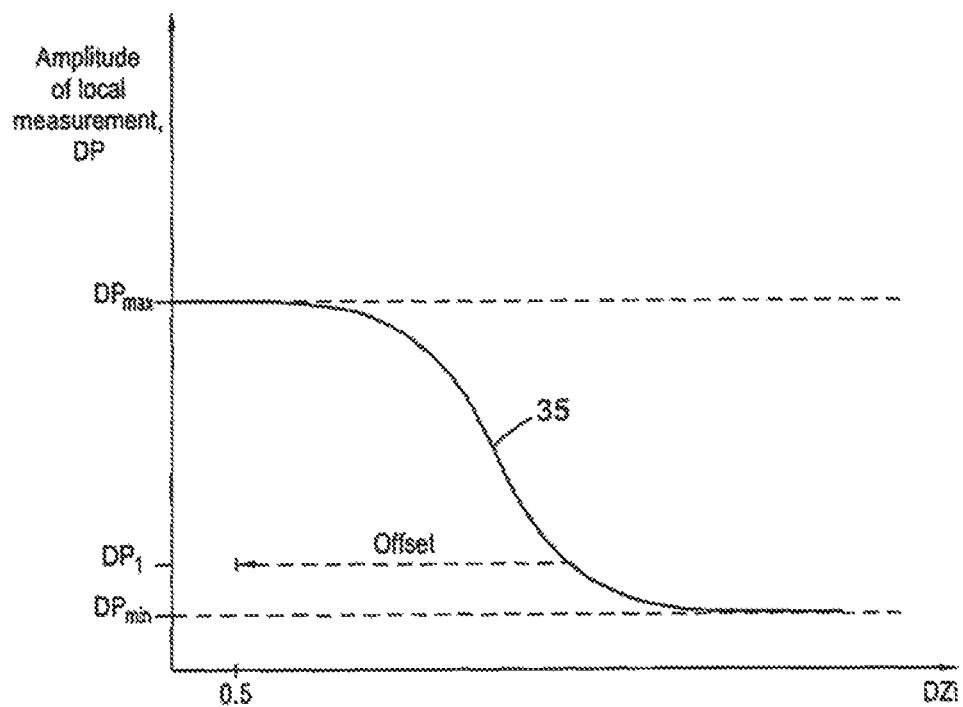
FIG. 4 is a graphical representation of a depletion master curve.

The depletion of the local concentration of target entity 24 as the sample flows from one chamber 8 to the next can be thought of as establishing a portion of a master depletion curve 35, which is illustrated in FIG. 4, with the starting concentration of the sample defining the portion. The master depletion curve 35 characterizes the variation in a local measurement indicative of the concentration of target entity 24 at the surface 20 of each of a respective chamber 8 against a quantity indicative of the amount of probe entities upstream of the position of the chamber 8 in the sequence.

The master depletion curve 35 may be understood conceptually by considering a hypothetical system having an unlimited number of notional chambers (and hence detection zones) into which a sample having a very high concentration of target entities is introduced. As the sample is introduced into the assay assembly, the initial chambers in the sequence are saturated with target entities, hence a measurement signal saturates at a maximum amplitude of the local measurement, $DP_{max}$. As the sample flows through the sample chambers in sequence the amount of target entities becomes successively depleted and the amplitude of the local measurements at each chamber decreases. As the sample flows through further chambers the amount of target entities is further depleted, the amplitude of the local measurements reaches a minimum amplitude, $DP_{min}$. The local measurements for the remaining notional chambers are then approximately constant at this minimum amplitude.

The master depletion curve 35 may be understood by considering experimental or hypothetical data from a plurality of experiments carried out at different starting target entity concentrations of the sample using assay assemblies having fixed depletion characteristics. Depletion characteristics are determined by factors including fluidic characteristics, for example the flow rate of sample through the assay assembly 6, the height and width of the chambers 8, and the length of the detection circuit; characteristics of the recognition layer, for example, the density of probe entities 22, the avidity and affinity of the probe entities 22 for the target entities 24; and characteristics of the target entity 24, for example the diffusion coefficient; amongst others. An assay assembly used to carry out the experiments typically has 5-10 chambers, accordingly the depletion data obtained will be representative of only a section of the master depletion curve, as explained above.

Figure 5:
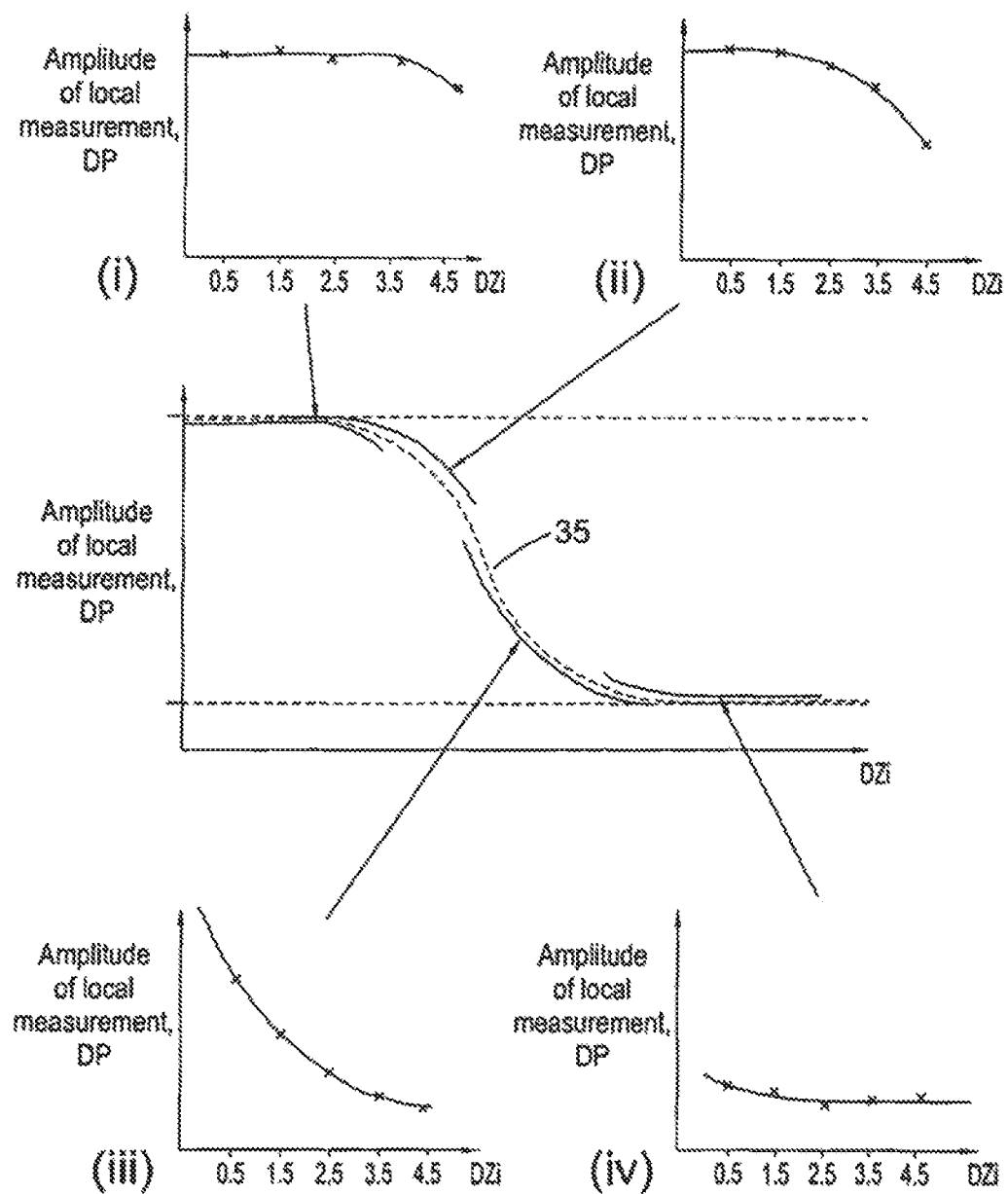
FIG. 5 is a graphical representation of the depletion curve of FIG. 4 is using experimental data.

With reference to FIG. 5, the master depletion curve may further be understood as a curve combining data from real or notional experiments carried out at a range of known starting concentrations. The data obtained may be thought of as being 'stitched' together to form the master depletion curve. If the experimental data sets 'overlap' where certain chambers in separate experiments have the same or similar local target concentrations, the data sets may be notionally 'shifted' along the x axis until a smooth line is obtained.

In the example illustrated in FIG. 5, the master depletion curve may be thought of as a combined depletion curve from four experiments, (i)-(iv). Each experiment is carried out using an assay assembly comprising five chambers and so a data set comprising five data points is obtained from each experiment. The starting concentration of target entity used in experiment (i) is higher than that used in (ii), which is in turn higher than that used in (iii), which is higher than that used in (iv). Using knowledge of the starting concentration of each experiment, the data sets can be 'stitched' together to form the master depletion curve.

The master depletion curve is represented by a parameterized function. In a specific embodiment, the function is a logistic function.

The parameterized function models the amplitude of local measurements, DP, made at a respective chamber against a quantity, $DZ_i$, indicative of the position in the sequence of the chamber 8 and hence detection zone or area, more specifically, the amount of probe entities upstream of the position of the chamber 8, i, in the sequence. In some embodiments the position and amount quantities are essentially the same, save for some scaling. In other embodiments where the amount for each chamber is not constant, the relationship may be more complicated as illustrated below.

Example values of $DZ_i$ are shown in Tables 1, 2, 3 and 4 below where '#DZ' is the position of the chamber (hence detection zone) in the sequence, 'DZ capacity' is the relative capacity of the chamber to bind to target entities, and '$DZ_i$' is the value indicative of the amount of probe entities upstream of the position of the chamber, i, in the sequence (which is of course also indication of the position in the sequence). $DZ_i$ is used in the parameterised function. In each of the examples shown in Tables 1-4, detection is made in the centre of the each chamber. Table 1 shows the case where the chambers each have the same relative capacity for binding target entities (for example the same amount of probe entities above to bind target entities). In this example, the values of $DZ_i$ used are 0.5, 1.5, 2.5, 3.5 and 4.5 (the 0.5 offset being representative of binding occurring in each chamber upstream of the detection area).

TABLE 1

| | #DZ | | | | |
|---|---|---|---|---|---|
| | 1 | 2 | 3 | 4 | 5 |
| DZ Capacity | 1 | 1 | 1 | 1 | 1 |
| DZi for fit | 0.5 | 1.5 | 2.5 | 3.5 | 4.5 |

Table 2 shows the case where the relative capacity of the chamber doubles from one chamber to the next. This difference in the relative capacity of the chambers is accounted for in the value of $DZ_i$ used.

TABLE 2

| | #DZ | | | | |
|---|---|---|---|---|---|
| | 1 | 2 | 3 | 4 | 5 |
| DZ Capacity | 1 | 2 | 4 | 8 | 16 |
| DZi for fit | 0.5 | 2 | 5 | 11 | 23 |

Table 3 shows the case where the $1^{st}$, $4^{th}$ and $5^{th}$ chambers have a relative capacity of 1 and the $2^{nd}$ and $3^{rd}$ chambers have a relative capacity of 2. Again, this difference in relative capacity is accounted for by adjustment of $DZ_i$.

TABLE 3

| | #DZ | | | | |
|---|---|---|---|---|---|
| | 1 | 2 | 3 | 4 | 5 |
| DZ Capacity | 1 | 2 | 2 | 1 | 1 |
| DZi for fit | 0.5 | 2 | 4 | 5.5 | 6.5 |

The chambers may be connected by microfluidic circuitry. In some embodiments, chambers are connected by microfluidic circuitry, the circuitry between the chambers having a binding capacity for target entities. Table 4 above shows the case where the assay areas have a relative binding capacity of 1 and the circuitry between the chambers have a relative capacity of 0.5. Detection is not carried out in the circuitry. In this case, $DZ_i$ is adjusted according to Table 4 to account for the relative capacity of the system.

TABLE 4

| | #DZ | | | | |
|---|---|---|---|---|---|
| | 1 | 2 | 3 | 4 | 5 |
| DZ Capacity | 1 | 2 | 2 | 1 | 1 |
| DZi for fit | 0.5 | 2.5 | 5 | 7 | 8.5 |

The parameterized function comprises constants which relate to the assay assembly and its depletion characteristics, $DP_{max}$ and Shape, and which are fixed for a given assay assembly and assay. The function also comprises a parameter dependent on the concentration of target entities 24 in the sample, Offset, which is indicative of the starting concentration of a sample. The parameter, Offset, is determined by fitting the parameterised function to the data points for each experiment carried out.

In the above notional and illustrative explanation, Offset determines the location of the data points for the actual chambers/detection areas on the master depletion curve.

With reference to FIG. 4, Offset can be understood as a value indicative of the extent to which the master depletion curve is shifted along the x axis. For example, for a sample having a low target concentration, the local measurement obtained at the first chamber in the sequence is a correspondingly low measurement, $DP_1$. For the master depletion curve to fit this experimental data it must be shifted such that the local measurement, $DP_1$, corresponds to the value of $DZ_i$, which is indicative of the first chamber, i=1. This is shown by $DZ_1$=0.5 in FIG. 4. The amount by which the master depletion curve must be shifted, and in which direction, in order to fit the assay data obtained will depend on the target concentration of the sample. Accordingly, the value of Offset is determined by fitting the parameterised function, and hence the master depletion curve, to the respective local measurements obtained at each chamber in the assay assembly.

The parameterised function is given by the expression shown in equation (5) below.

$$DP = \frac{2 \times DP_{max}}{1 + \exp[Shape \times (DZ_i + \text{Offset})]} \quad (5)$$

As described above with respect to FIG. 4, $DP_{max}$ is the maximum amplitude of the local measurement which can be obtained at a first chamber 8 of an assay assembly and remains constant throughout an experiment. The parameter Shape is indicative of the rate at which the concentration of target entities at the chamber surface is depleted as the sample flows from one chamber to the next. This value depends on the depletion characteristics of the assay assembly and remains constant throughout an experiment for a given assay assembly and assay. exp is typically euler's number, e, however any other suitable base may be used with a corresponding adjustment in the other parameters.

As explained above, $DZ_i$ corresponds to a value indicative of the amount of probe entities upstream of the position of the respective chamber, i, in the sequence. With reference to FIG. 2A, the detection zone 30 for each chamber 8 is a portion at the centre of the chamber surface 20. Accordingly in this arrangement, for each chamber, $DZ_i$ may take a positive half integer value i.e. 0.5, 1.5, 2.5, 3.5 etc. Alternatively, $DZ_i$ may take an integer value, or any other suitable value indicative of the amount of probe entities upstream of the position of the chamber in the assay assembly.

The constants Shape and $DP_{max}$ are determined by characterizing a batch of assay assemblies prior to carrying out an experiment to determine a sample concentration. Each assay assembly is only used once and hence experiments to characterise a batch of assemblies are carried out using respective assay assemblies from the same manufacturing batch to characterise the batch of microfluidic devices 2. The determined values of Shape and $DP_{max}$ are verified as being representative of the batch by validation experiments using other assemblies of the batch with samples of known sample concentration or target entities. The determined values are then associated with the microfluidic devices 2, for example, by shipping with the device 2, for example as an indication on packaging, or marking the device itself 2 to indicate the values, for example using a bar code or other suitable means for carrying this information. The packaging and/or disc may carry this information directly or may carry a link to a remote location where this information is held for access over a network for example the internet.

These values are constant for the assay assembly across all the respective local measurements. $DP_{max}$ and Shape, which are collectively denoted by $\lambda$, are determined using known experimental data obtained from a plurality of experiments, j, each having a known starting concentration of target entities (the concentrations spanning a range of concentrations of interest) and each carried out using an assay assembly having a plurality of assay areas, i. $DP_{max}$ and Shape are determined by minimizing the following sum:

$$\sum_{j=1}^{m} \sum_{i=1}^{n} [DP(DZ_i) - f_\lambda(DZ_i + \text{Offset})]^2 \quad (6)$$

where $DP(DZ_i)$ is the local measurement at the assay area, i, and $f$ is the corresponding value of the parameterized function having constants $\lambda$. Data from m experiments is used, each experiment having been carried out using an assay assembly having n assay areas. In some embodiments, the parameters of Shape and $DP_{max}$ are determined using any suitable optimization technique, e.g. least square, gradient descent, regression or Chi-squared minimization techniques. From the sum, (6), above, 'Offset' is also determined for each of the plurality of experiments, j, hence a relationship between 'Offset' and the starting concentration of target entities is determined. This relationship between $\text{Offset}_j$ and concentration, $\text{Concentration}_j$, for each of the plurality of experiment, j, defines data points $\{\text{Concentration}_j, \text{Offset}_j\}$ that can be used to fit a calibration function. As will be described further below, this calibration function is used to determine the sample concentration based on the value of Offset.

Using an assembly from a batch that has been characterized (values for $\lambda$ determined) assay experiments to find unknown concentrations of target entities in a sample are carried out. The value of Offset is fit to the assay data from a given experiment in order to provide an indication of the starting concentration of the sample. For the avoidance of doubt, reference herein to the 'starting concentration' should be understood as referring to the concentration of target entities in a sample to be tested. The parameterized function may be fit to the assay data and the value of Offset determined by minimizing the following sum:

$$\sum_{i=1}^{n} [DP(DZ_i) - f(DZ_i + \text{Offset})]^2 \quad (7)$$

where $DP(DZ_i)$ is the local measurement at the assay area, i, and $f$ is the corresponding value of the parameterized function. Minimization of this or any suitable cost function can be carried to obtain the best fit of the parameterized function to the assay data. In some embodiments, least-square regression minimization techniques are used and validated using a chi-squared test.

Once the value of Offset has been determined by fitting the parameterized function to the experimental data obtained, a value indicative of the starting target concentration of the sample can be determined using a calibration function.

The calibration function comprises a first function and a second function. The first function, $f_1$, is used to determine the target concentration for samples where the target concentration is known to be high and is a function of 'Offset', for example $f_1$ may be found by fitting a suitable function to the data points, $\{\text{Concentration}_j, \text{Offset}_j\}$, described above. The second function, $f_2$, is used to determine the target concentration for samples where the target concentration is known to be low and is a function of the undepleted measurement that would be obtained by the system, in other words, a function of the hypothetical local measurement when $DZ_i=0$. Accordingly, the second function is a function of the expression (8) below:

$$\frac{2 \times DP_{max}}{1 + \exp[\text{Shape} \times \text{Offset}]} \quad (8)$$

In some embodiments, the first and second functions are represented in the form of an exponential function as shown by equations (9a) and (9b) below.

$$f_1 = X_1 + Y_1 \exp[-Z_1 \times \text{Offset}] \quad (9a)$$

$$f_2 = X_2 + Y_2 \exp[+Z_2 \times DP(DZ_i=0)] \quad (9b)$$

$DP(DZ_i=0)$ is the amplitude of the local measurement when $DZ_i=0$. The parameters $X_{1,2}$, $Y_{1,2}$ and $Z_{1,2}$ are be obtained by fitting to experimental data in a similar manner as described above.

In some embodiments, determining the sample concentration is an iterative process. For example, a first step may be applied initially followed by a second step that provides a more refined result. Specifically, in some embodiments, the first function is used in the first step to determine a value indicative of concentration. If the value is below a threshold, the second step re-calculates the value using the second calibration function. In some embodiments, the order is reversed and the first function is used in the second step if the value from the first step (from the second function) is above a threshold.

Alternatively, in some embodiments the calibration function is a single function relating Offset to the target concentration of the sample.

In some embodiments, the calibration curve of sample concentration against Offset is a logistic function e.g. a 4PL nonlinear regression model. In the case of a 4PL model, the sample concentration is a function of (Offset, a, b, c, d), where a, b, c and d are parameters of the model which may be obtained using minimization techniques, for example Chi-squared minimization techniques, and experimental data as described above.

Figure 6:
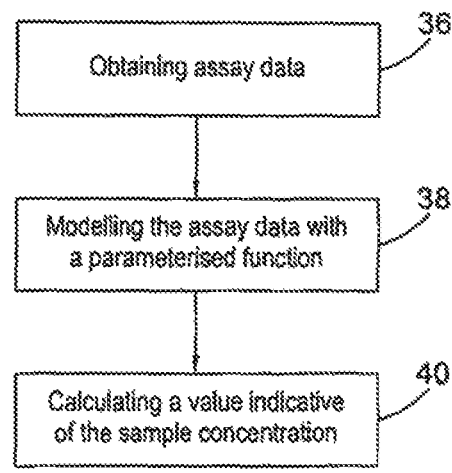
FIG. 6 is a flow chart showing a method for determining the concentration of a target entity in a sample.

A method for determining the concentration of target entities in a sample will now be described in overview with reference to FIG. 6. In a first step 36 assay data is obtained. The assay data obtained comprises a plurality of data points, each data point corresponding to a local measurement carried out at a respective chamber 8. The local measurements relate to the detection of changes in a refractive index at the surface of each of the respective chambers and are indicative of the concentration of target entity 24 at the surface 20 of the respective chamber 8. The assay data is modeled with the parameterized function at a second step 38, as described above, the parameterized function comprising the parameter, Offset, dependent on the concentration of the target entity in the sample. A value indicative of the concentration of the target entity in the sample is then determined at a third step 40 based on 'Offset' using the first and second calibration functions described above. It will be understood that at some point prior to step 38, for example when loading the device 2 into the system 26, the parameters λ are loaded into the system, for example by manual entry or by reading a tag, such as a barcode, carrying this information, as described above.

Figure 7:
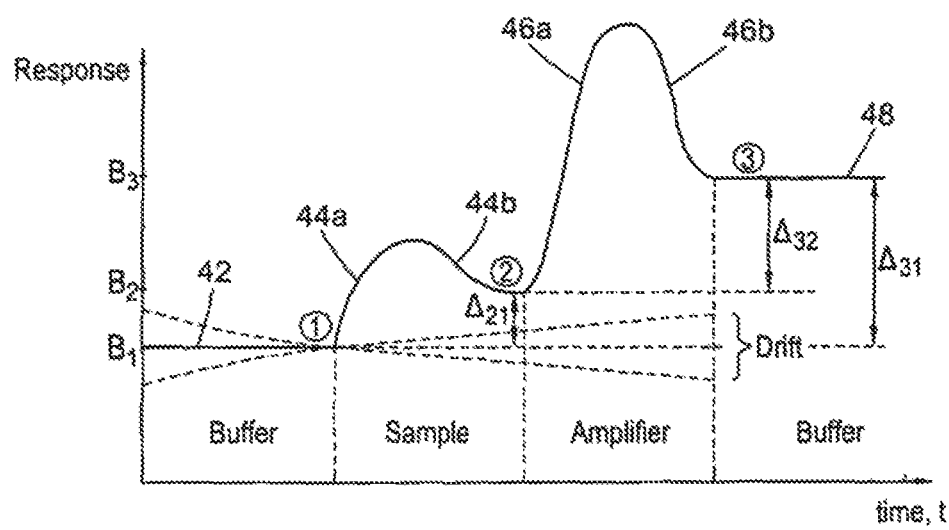
FIG. 7 is a sensorgram illustrating the variation in a response amplitude with time and illustrating local measurements $\Delta_{31}$, $\Delta_{32}$ and $\Delta_{21}$.

The system 26 described above and shown in FIG. 3 is used to obtain assay data. Firstly a buffer solution is made to flow through into the assay assembly 6 as a baseline, followed by a sample to be tested, an amplifier solution, and finally a wash with a second buffer solution. With reference to FIG. 7, for each respective chamber 8, changes in the refractive index at the chamber surface 20 can be detected by the detector 32 such that the amplitude of the detected signal, for example change in the angle at which surface plasmon resonance occurs, increases in direct proportion to the magnitude of the change in refractive index at the chamber surface 20.

For each respective chamber 8, once the buffer solution has flowed through the chamber 8, a baseline measurement 42 is measured for the detection region 30. The sample comprising an amount of target entities 24 is then introduced into the chamber 8. As the target entities 24 bind to probe entities 22 at the surface 20 of the chamber, the refractive index at the surface 20 changes and consequently the amplitude of the measured signal for the detection region 30 increases 44a. In some cases, a proportion of the target-probe binding is reversible hence a reduction 44b in the amplitude of the measured signal for the detection region 30 may occur until a steady state is reached. Such reduction may not be observed in cases where the concentration of target entity 24 in the sample is very high.

Figure 2B:
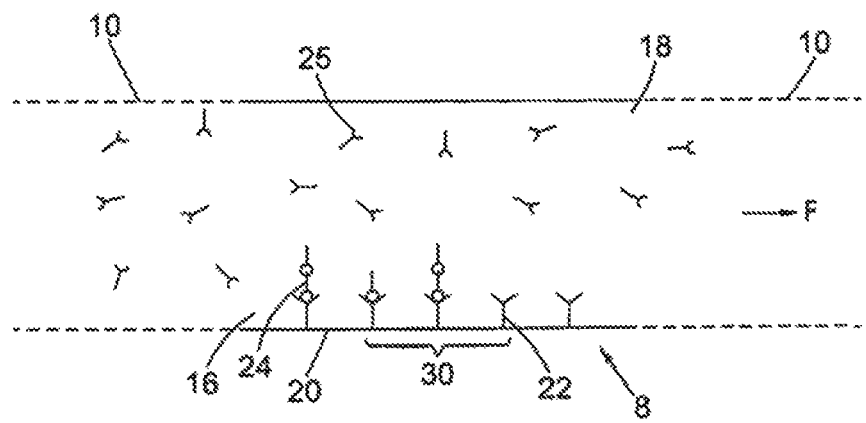
FIG. 2B is schematic illustration of a cross-sectional view of amplifier-target binding an assay area of the assay assembly of FIG. 1.

With reference to FIG. 2B and FIG. 7, the amplifier solution is then made to flow through the chamber 8. Active components 25 in the amplifier solution bind to the target entities 24 which are in turn bound to the probe entities 22. A sufficiently high concentration of amplifier is made to flow through the chamber 8 such that the bound target entities are saturated with amplifier.

This results in a further change to the refractive index at the surface 20 of the chamber 8 and consequently the amplitude of the measured signal for the detection region 30 increases 46a. As with the target-probe binding, in some cases a proportion of the amplifier-target binding is reversible hence a reduction 46b in the amplitude of the measured signal for the detection region 30 may occur until a steady state is reached. Such reduction may not be observed in cases where the concentration of active component in the amplifier is very high.

Finally the second buffer solution is made to flow through the chamber 8 to wash away any remaining unbound sample or amplifier. Consequently, the amplitude of the measured signal for the detection region 30 remains constant 48. The local measurements may be any of a number of suitable measurements, some of which are described in more detail in the embodiments below.

Alternatively, assay data may be obtained via any other suitable means, or may be obtained from a previously run assay, possibly run by a third party.

Once the assay data has been obtained it is modeled with the parameterized function and a value of 'Offset' is determined as described above. The constants $DP_{max}$ and Shape characteristic of the assay assembly having been previously determined using the method described above and having been marked on the microfluidic device itself, for example using a bar code. The parameterized function models the local measurements carried out at each respective chamber 8 against the quantity, DZ. The quality of fit of the measured data to the parameterized function is evaluated, for example by calculation of Pearson's coefficient for the fit, using Chi-squared minimization techniques or using any other suitable means. The quality of the fit is compared to a predetermined threshold such that, if the quality of fit is not sufficiently good to meet the threshold, the data is discarded.

Once the value of Offset has been determined by fitting the parameterized function to the assay data obtained, a value indicative of the target concentration of the sample can be determined using the calibration function as outlined above.

Embodiment 1

In a first embodiment, local measurements are carried out at each of the respective chambers 8 in the assay assembly by detecting the amplitude of the baseline response obtained prior to a sample being made to flow through the chamber 8, $B_1$, shown as detection point 1 on FIG. 7, detecting the amplitude of the response following flow of the second buffer through the chamber 8, $B_3$, shown at detection point 3 on FIG. 7, and determining a difference between the two responses, $\Delta_{31}=B_3-B_1$.

The parameterized function for each respective local measurement is therefore given by equation (10) below.

$$\Delta_{31} \cong \frac{2 \times DP_{max\_amp}}{1+\exp[\text{Shape} \times (DZ_i + \text{Offset})]} \qquad (10)$$

Where $DP_{max\_amp}$ is the maximum amplitude of the local measurement at a chamber 8 following interaction of the amplifier with the chamber 8. In this case, since measurements $B_1$ and $B_3$ are each made when the bulk solution in the chamber is buffer solution (i.e. the bulk solution at each measurement has the same refractive index), as $DZ_i$ becomes larger, DP will tend towards zero hence the amplitude $DP_{min}$ of the master curve/parameterised function is zero.

Embodiment 2

A potential drawback with the approach outlined in Embodiment 1 is that there can be drift in the signals being compared, for example, due to fluctuations in temperature, vibrations in the system etc. In the example of Surface Plasmon Resonance, the signal is dependent on the local refractive index near the detection surface. Such a signal therefore comprises contributions from (i) the probe/target layer having a certain density of target entities bound thereto; (ii) the surrounding liquid; (iii) the metal present at the surface of the chamber e.g. gold. The refractive index of these three contributions is dependent on the temperature and so drifts in temperature will cause drift in the signal detected. Similar drift effects result from mechanical vibrations in the system.

This is shown on FIG. 7. As a result of this drift, the noise level in the system is higher and the detection capability decreases as a result. To overcome this, a local measurement $\Delta_{32}$ can be used instead of $\Delta_{31}$, as will now be described.

Local measurements, $\Delta_{32}$, are carried out at each of the respective chambers 8 in the assay assembly. $\Delta_{32}$ is measured by detecting the amplitude of a response, $B_2$, following interaction of the sample with the chamber surface 20 and prior to interaction of the amplifier with target entities bound to the surface, shown as detection point 2 in FIG. 7. The amplitude of the response following introduction of the second buffer into the chamber 8, $B_3$, is then detected shown as detection point 3 on FIG. 7, and a difference between the two responses, $\Delta_{32}=B_3-B_2$ is determined.

Measuring $\Delta_{32}$ this has the advantage that the measurement is made over a shorter time period (because the time between $B_2$ and $B_3$ is shorter than the time between $B_1$ and $B_3$) and so the effect of drift is reduced.

When $B_2$ is detected the bulk material in the chamber 8 is the sample, whereas when $B_3$ is detected the bulk material in the chamber 8 is buffer solution. The sample and the buffer solution each have a different refractive index, therefore the local measurement, $\Delta_{32}$, comprises a contribution caused by the change in the bulk material from sample to buffer solution between $B_2$ and $B_3$. Accordingly, $\Delta_{32}$ can be represented by equation (11) shown below.

$$\Delta_{32}=f(\text{Offset})+\Delta_{bulk} \qquad (11)$$

Where $f(\text{Offset})$ is the parameterized function/master curve and $\Delta_{bulk}$ is the contribution due to the refractive index of the sample.

Where the sample is blood, for example, the change in the refractive index due to the difference in bulk solution between $B_2$ and $B_3$, $\Delta_{bulk}$, will vary from person to person and is accordingly is unknown quantity.

$\Delta_{bulk}$ can be obtained as a further variable parameter by fitting the function (11) to the experimental data, that is adjusting Offset and $\Delta_{bulk}$ at the same time. Alternatively, with reference to FIG. 7, $\Delta_{21}$ can be measured, as will be described below, and used as an approximation to $\Delta_{bulk}$ (ignoring the effect of unamplified target-probe binding). $\Delta_{21}$ is measured by detecting the amplitude of the baseline response, $B_1$, once buffer solution has flowed through the assay assembly, detecting the amplitude of a response, $B_2$, following interaction of the sample with the chamber surface 20 and prior to interaction of the amplifier with target entities bound to the surface, and determining a difference between $B_1$ and $B_2$, i.e. $\Delta_{21}=B_2-B_1$. The measurement $\Delta_{21}$ can be thought of according to equations (12) below.

$$\Delta_{21}=\Delta_{unamplified\_binding}+\Delta_{bulk} \qquad (12)$$

Where $\Delta_{unamplified\_binding}$ is the contribution due to the unamplified binding of target entities to the surface of the chamber. Since the contribution to the signal from the bulk is much greater than the contribution from the unamplified binding of target entities to the surface of the chamber, measurement $\Delta_{21}$ can be considered as approximately equal to $\Delta_{bulk}$. Accordingly, in some embodiments, $\Delta_{32}-\Delta_{21}$ can be used as the local measurements, i.e. the local measurements are modeled as $\Delta_{32}-\Delta_{21}=f(\text{Offset})$. Of course, it is equivalent to model $\Delta_{32}=\Delta_{21}+f(\text{Offset})$ and this is done instead in some embodiments.

Embodiment 3

In another embodiment, a change of the amplitude of the response signal detected by the detector 32 as the amplifier flows across the surface 20 of the chamber 8, $G_{amp}$, is used as the local measurement. This measurement reflects the rate at which the active components in the amplifier bind with target entities 24 bound to the respective chamber 8.

The master depletion curve shown in FIG. 4 and described above also applies in this case where the local measurement is $G_{amp}$, and the corresponding model is $G_{amp}=f(\text{Offset})$, with $f$ defined as discussed above, albeit with its parameters adapted accordingly, for example, $DP_{max}$ being the notional maximum rate of change for a saturated chamber 8.

Figure 8:
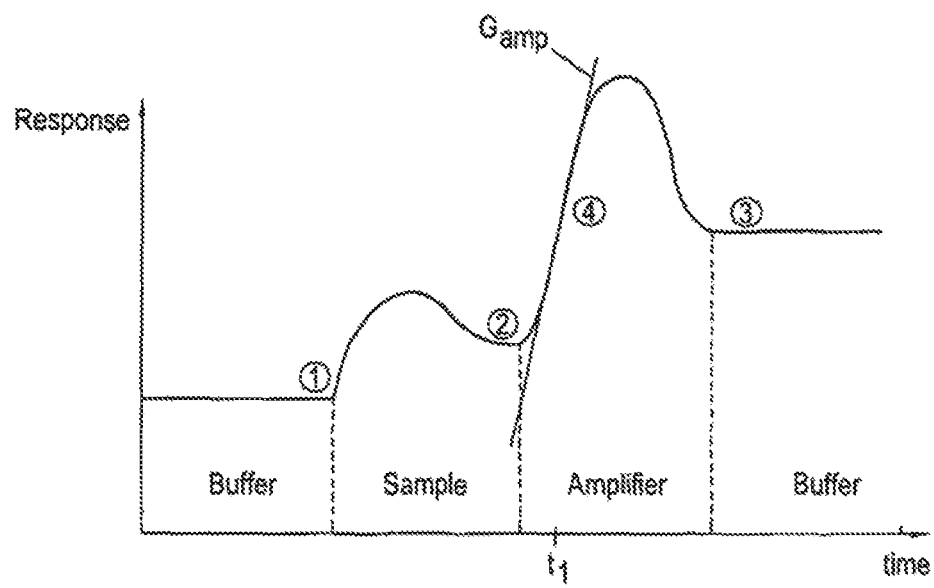
FIG. 8 is a sensorgram illustrating the variation in a response amplitude with time and illustrating a local measurement $G_{amp}$.
Figure 9:
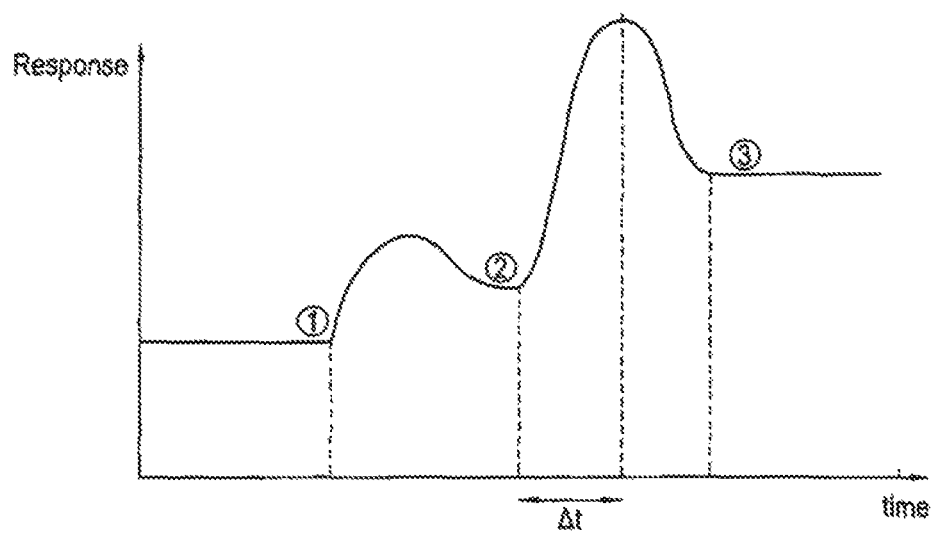
FIG. 9 is a sensorgram illustrating the variation in a response amplitude with time and illustrating a local measurement $\Delta_r$.

In the example shown in FIG. 8, $G_{amp}$ equates to the gradient of the curve at time $t_1$, indicated by point 4 on the sensorgram. Of course, any other suitable, for example amplification, rate dependent measurement may also be taken.

Embodiment 4

In yet another embodiment, a time taken from introduction of the amplifier into the respective chamber to detection of a threshold amplitude of the response signal or a feature of the signal (e.g. a maximum) is measured. By using $1/\Delta_t$ as the local measurement, the master depletion curve shown in FIG. 4 and described above also applies and the experimental data can be modeled as $1/\Delta_t = f(\text{Offset})$, with $f$ defined as above, albeit with its parameters adjusted accordingly, e.g. $DP_{max}$ being the notional maximum value of $1/\Delta_t$ (minimum of $\Delta_t$) for a saturated chamber 8.

Of course, any other suitable time dependent measurement may also be taken.

Using the same system and method as described above and taking any suitable local measurement, when the concentration of the active component in the amplifier is not sufficiently high to saturate the assay assembly, the local measurements are also dependent on this active component concentration which will deplete as the amplifier flows from one chamber to the next. The parameterized function is therefore arranged to account for this dependency. For example, the parameterized function may contain an additional parameter to account for the depletion in the active component concentration. Alternatively or in addition, the 'Shape' parameter may be a vector varying with both the sample concentration and amplifier concentration. In some embodiments, the effect of the concentration of amplifier can be thought of as being akin to the effect of the density of probe entities present in the assay assembly as a first approximation. Accordingly, for example, the value of $DZ_i$ may be adjusted to account for the amplifier concentration in a similar way to how $DZ_i$ is adjusted to take into account the relative binding capacity of the assay assembly as described in detail above.

In general, if amplifier concentrations are non-saturating, two depletion effects occur: 1) depletion of target entities; 2) depletion of amplifier. (2) will depend on the concentration of target entities at each detection area. The overall effect will depend on the combination of these two effects. Each effect is, in some embodiments, assessed independently and a higher-order function is used to combine both effects. Alternatively, both effects may simply be captured by using a suitable higher-order function and/or a function with more parameters for fitting the depletion characteristics (e.g. a 4PL or 5PL function).

It will be understood that whether or not the amplifier is provided in a saturating concentration is independent of the local measurement used and a non-saturating amplifier concentrations may be used with any of local measurements identified in the embodiments described above or indeed any other local measurement.

It will be understood that the above description is of specific embodiments by way of example only and that many modifications and alterations will be within the skilled person's reach and are intended to be covered by the scope of the appendent claims. For example, whilst the description above has been set out in terms of detection of changes in surface plasmon resonance, it will be appreciated that any other suitable means for quantitatively detecting an amount of target-probe binding at the surface 20 may be used, for example, UV absorption fluorescence of the target entity 24 and/or detection of a label bound to the target entity 24 may be used. In some embodiments, a plurality of detection zones is provided in a single chamber, for example with detection areas from which signals are measured spaced along a strip of functionalized surface.

The invention claimed is:

1. A method for determining a sample concentration of target entities in a sample, the method comprising:
   obtaining assay data comprising data points of respective local measurements indicative of a local concentration of the target entities at each of a plurality of assay areas of an assay assembly, wherein the assay areas are connected in series such that a sample flowing through the assay assembly flows past each assay area in sequence, and wherein each assay area comprises a plurality of probe entities immobilized at a surface of the assay area, the probe entities being arranged to bind to the target entities in the sample, such that the concentration of the target entities is depleted as the sample flows from one of the assay areas to the next;
   modeling the assay data with a parameterized function, wherein the parameterized function is a logistic function that is proportional to $$\frac{DP_{max}}{1 + \exp[\text{Shape} \times (DZ_i + \text{Offset})]}$$

wherein $DP_{max}$ and Shape are fixed parameters of the assay assembly, Offset is a parameter dependent on a sample target concentration, and $DZ_i$ is a quantity indicating the position of the respective assay area, i, in a sample flow sequence; and
   determining a value related to the sample concentration based on the Offset parameter, whereby the value related to the sample concentraton allows the sample concentration of target entities in the sample to be determined.

2. A method according to claim 1, wherein the parameterized function is derived from assay data sets obtained for a range of sample concentrations.

3. A method according to claim 1, wherein one of the one or more parameters is indicative of an offset amount which offsets the quantity indicative of the position of the assay area in the sample flow sequence such that the parameterized function is a function of the local measurements against the quantity indicative of the position of the assay area in the sequence, offset by the offset amount.

4. A method according to claim 3, wherein the offset amount is determined by minimizing a difference between the respective local measurement and a corresponding value of the parameterized function for each assay area of the assay assembly.

5. A method according to claim 1, wherein the parameterized function is characteristic of the assay assembly.

6. A method according to claim 5, wherein the parameterized function is at least in part defined by one or more fixed parameters characteristic of the assay assembly.

7. A method according to claim 6, wherein the one or more fixed parameters are determined from data sets of local measurements against the quantity obtained for respective sample target concentrations spanning a range of sample target concentrations.

8. A method according to claim 1, comprising determining the value based on at least one of the one or more parameters using a calibration function, wherein the calibration function comprises a first function for use at sample concentrations of target entities above a given value, and a second function for use at sample concentrations of target entities below the given value.

9. A method according to claim 1, wherein the value related to the sample concentration is determined using a calibration function and wherein the calibration function comprises a first function for use at sample concentrations of target entities above a given value, and a second function for use at sample concentrations of target entities below the given value, wherein the first function is a function of Offset, and the second function is a function of:

$$\frac{DP_{max}}{1 + \exp[\text{Shape} \times \text{Offset}]}.$$

10. A method according to claim 1, wherein each local measurement is indicative of a variation in a refractive index at the surface of the respective assay area.

11. A method according to claim 10, wherein the refractive index at the surface of the respective assay area is determined based on the detection of a change in Surface Plasmon Resonance.

12. A method according to claim 10, wherein the variation in the refractive index at the surface of the respective assay area is amplified by an amplifier solution flowing past the respective assay area, wherein the amplifier solution is arranged to interact with target entities bound to the surface of the assay area such that the variation in the refractive index at the respective assay area is amplified when the amplifier has interacted with the bound target entities.

13. A method according to claim 12, wherein each local measurement comprises a difference between a pre-amplification signal and post-amplification signal, wherein the pre-amplification signal has been detected after interaction of the sample with the respective assay area and before interaction of the amplifier solution with target entities bound to the respective assay area, and the post-amplification signal has been detected after interaction of the amplifier solution with target entities bound to the respective assay area.

14. A method according to claim 13, wherein modeling the assay data comprises using an adjustment term to account for a bulk refractive index of the sample.

15. A method according to claim 14, wherein the adjustment term is determined based on a difference between a baseline signal detected prior to interaction of the sample with the assay area and the pre-amplification signal.

16. A method according to claim 12, wherein each local measurement indicates a rate at which the amplifier solution interacts with the respective assay area.

17. A method according to claim 12, wherein each local measurement comprises a measurement indicative of the time taken from introduction of the amplifier solution into the respective assay area to detection of a signal feature, for example a maximum or threshold signal amplitude.

18. A method according to claim 1, wherein an amount of probe entities with target entities between each pair of the plurality of assay areas is substantially constant.

19. A method according to claim 1 where the quantity indicating the position of the assay area in the sequence indicates an amount of probe entities upstream of the position of the assay area.

20. A method according to claim 1, wherein each assay area is connected to the next assay area in the sequence via a conduit.

21. A method according to claim 1, wherein obtaining assay data comprises:
introducing a sample into the assay assembly;
causing the sample to flow through the assay assembly; and
carrying out local measurements at each assay area.

* * * * *